(12) United States Patent
Ku et al.

(10) Patent No.: US 8,536,152 B2
(45) Date of Patent: Sep. 17, 2013

(54) METHODS OF USING DIACEREIN AS AN ADJUNCTIVE THERAPY FOR DIABETES

(75) Inventors: Mannching Sherry Ku, Thiells, NY (US); Danchen Gao, Long Grove, IL (US); Wei-Shu Lu, Tucheng (TW); Chih-Ming Chen, Taipei (TW); I-Yin Lin, Taipei (TW)

(73) Assignee: TWi Biotechnology, Inc., Taipei (TW)

( * ) Notice: Subject to any disclaimer, the term of this patent is extended or adjusted under 35 U.S.C. 154(b) by 77 days.

(21) Appl. No.: 13/081,548

(22) Filed: Apr. 7, 2011

(65) Prior Publication Data

US 2011/0251155 A1 Oct. 13, 2011

Related U.S. Application Data

(60) Provisional application No. 61/321,931, filed on Apr. 8, 2010.

(51) Int. Cl.
*A61K 31/715* (2006.01)

(52) U.S. Cl.
USPC .......................................... 514/54

(58) Field of Classification Search
USPC ............................................ 514/54
See application file for complete search history.

(56) References Cited

U.S. PATENT DOCUMENTS

| 2006/0252670 A1 | 11/2006 | Fiorucci et al. | |
| 2008/0207758 A1 | 8/2008 | Cong | |
| 2010/0104651 A1* | 4/2010 | Gao et al. | 424/489 |
| 2011/0045522 A1* | 2/2011 | Gao et al. | 435/29 |
| 2012/0232044 A1* | 9/2012 | Ku et al. | 514/171 |

OTHER PUBLICATIONS

Dinarello et al. Blocking IL-1: interleukin 1 receptor antagonist in vivo and in vitro. Immunol Today 12:404-410, 1991.*
Malaguti et al., "Diacerhein downregulate proinflammatory cytokines expression and decrease the autoimmune diabetes frequency in nonobese diabetic (NOD) mice", International Immunopharmacology, 2008, 8, pp. 782-791.

* cited by examiner

*Primary Examiner* — Wu-Cheng Winston Shen
*Assistant Examiner* — Yih-Horng Shiao
(74) *Attorney, Agent, or Firm* — Wood, Philips, Katz, Clark & Mortimer

(57) ABSTRACT

The present invention provides methods of treating type II diabetes using combinations of diacerein or its derivatives with other antidiabetic agents. The methods may also allow improving glycemic control of type II diabetes patients and/or reducing side effects and/or cardiovascular risks of antidiabetic agents.

23 Claims, 4 Drawing Sheets

Mean Change from Baseline in HbA1c

Mean Change from Baseline in Fasting Plasma Glucose

Mean Beta-Cell Function

METHODS OF USING DIACEREIN AS AN ADJUNCTIVE THERAPY FOR DIABETES

BACKGROUND OF THE INVENTION

Diacerein, [4,5-bis(acetyloxy)-9,10-dioxo-2-anthracene carboxylic acid]) is a highly purified anthraquinone derivative. It has been approved as a SYmptomatic Slow-Acting Drug in Osteoarthritis (SYSADOA) in several countries. Rhein is the major active metabolite of diacerein. Rhein has been shown to control the blood glucose concentration in type 2 (or type II) diabetes rodent models. However, no studies indicated that diacerein can control blood glucose in humans with type 2 diabetes. No literature has reported that diacerein can be used as adjunctive therapy for treating type II diabetes patients with inadequate drug response to current antidiabetic therapies.

The prevalence of diabetes has increased throughout the world. About seven percent of the population between 45-64 years old has diabetes and the number significantly increases in the population over 65 years old. There are two forms of diabetes. In the form of the disease known as type II, non-insulin dependent diabetes (NIDDM) or adult-onset (as opposed to juvenile diabetes or type I), it is a disorder which is characterized by high blood glucose in the context of insulin resistance and relative insulin deficiency. The pancreas in type II diabetic patients often continues to secrete insulin. However, this insulin is ineffective in preventing the symptoms of diabetes which include the rise of cardiovascular risk factors such as hyperglycemia, hypertension, hypertriglycemia, high serum low-density-lipoprotein (LDL) cholesterol concentrations, low serum high-density-lipoprotein (HDL) cholesterol concentrations, impaired carbohydrate metabolism, glycosuria, decreased insulin sensitivity, and centralized obesity. Many of these cardiovascular risk factors are known to precede the onset of diabetes by as much as a decade. The symptoms of type II diabetes have led to severe complications, including macrovascular complications (coronary artery disease, peripheral arterial disease, and stroke) and microvascular complications (retinopathy, nephropathy, and neuropathy). The importance of blood glucose control and maintenance of glycated hemoglobin A1C (HbA1c) below 7.0% in preventing diabetic complications is now recognized.

A number of antihyperglycemic agent classes, each with its unique mechanism of action, have been introduced during the past several years: sulfonylureas, bisguanides, alpha-glucosidase inhibitors, thiazolidinediones (TZDs), Dipeptidyl peptidase-4 inhibitors (DPP-4 inhibitors), nonsulfonylurea insulin secretagogues, glucagon-like peptide-1 analog and insulin. According to clinical guidelines, first line blood glucose lowering therapy of type II diabetes is metformin or sulfonylurea monotherapy. However, monotherapy with metformin or sulfonylurea is of limited benefit. Only about 44% of patients maintain HbA1c below 7% after receiving the treatment for three years, and only 13% of patients maintain the level after nine years. If first line treatment is unsatisfactory, patients are moved to second line combination therapies such as metformin with sulfonylurea. In patients failing monotherapy with either agent alone, only about 30% of the patients treated with the combination or second line therapy of metformin with sulfonylurea, achieve HbA1c below 7% after two years of treatment. If this kind of therapy is still insufficient for patients to control blood glucose, then DPP-4 inhibitors, thiazolidinedione, glucagon-like peptide-1 analogs, meglitinides, alpha-glucosidase inhibitors, and/or insulin can be added to the second line treatment.

Despite the existence of anti-diabetic drugs, some patients cannot achieve the treatment goals. Accordingly, there is still a need for a new agent which effectively improves glycemic control of type II diabetes.

SUMMARY OF THE INVENTION

The present invention relates to therapeutic methods of treating type II diabetes patients. The inventive methods are especially suitable for type II diabetes patients who have inadequate glycemic control with current antidiabetic therapy.

More specifically, the present invention provides methods of using diacerein or its derivatives for the treatment for type II diabetes.

In one embodiment, the invention provides a method of an adjunctive treatment for type II diabetes mellitus comprising administering to a subject with type II diabetes who has an inadequate response to an antidiabetic agent a therapeutically effective amount of diacerein or a pharmaceutically acceptable salt, an analog, a prodrug or an active metabolite thereof.

In yet another embodiment, the invention provides a method of improving glycemic control in a subject receiving at least one antidiabetic agent comprising administering to said subject: a) a therapeutically effective amount of diacerein or a pharmaceutically acceptable salt, a prodrug, an analog, or an active metabolite thereof, and b) said antidiabetic agent.

In another embodiment, the invention provides a method of a combinational treatment for type II diabetes mellitus comprising administering to a subject in need thereof: a) at least one antidiabetic agent, and b) a therapeutically effective amount of diacerein or a pharmaceutically acceptable salt, an analog, a prodrug or an active metabolite thereof.

In yet another embodiment, the invention provides a method for reducing a side effect of an antidiabetic agent administered to a diabetic patient comprising administering to said patient: a) a therapeutically effective amount of diacerein or a pharmaceutically acceptable salt, an analog, a prodrug, or an active metabolite thereof, and b) said antidiabetic agent.

In yet another embodiment, the invention provides a method for reducing a cardiovascular risk of an antidiabetic agent administered to a diabetic patient comprising administering to said patient: a) a therapeutically effective amount of diacerein or a pharmaceutically acceptable salt, an analog, a prodrug, or an active metabolite thereof, and b) said antidiabetic agent.

DETAILED DESCRIPTION OF THE INVENTION

Figure 1:
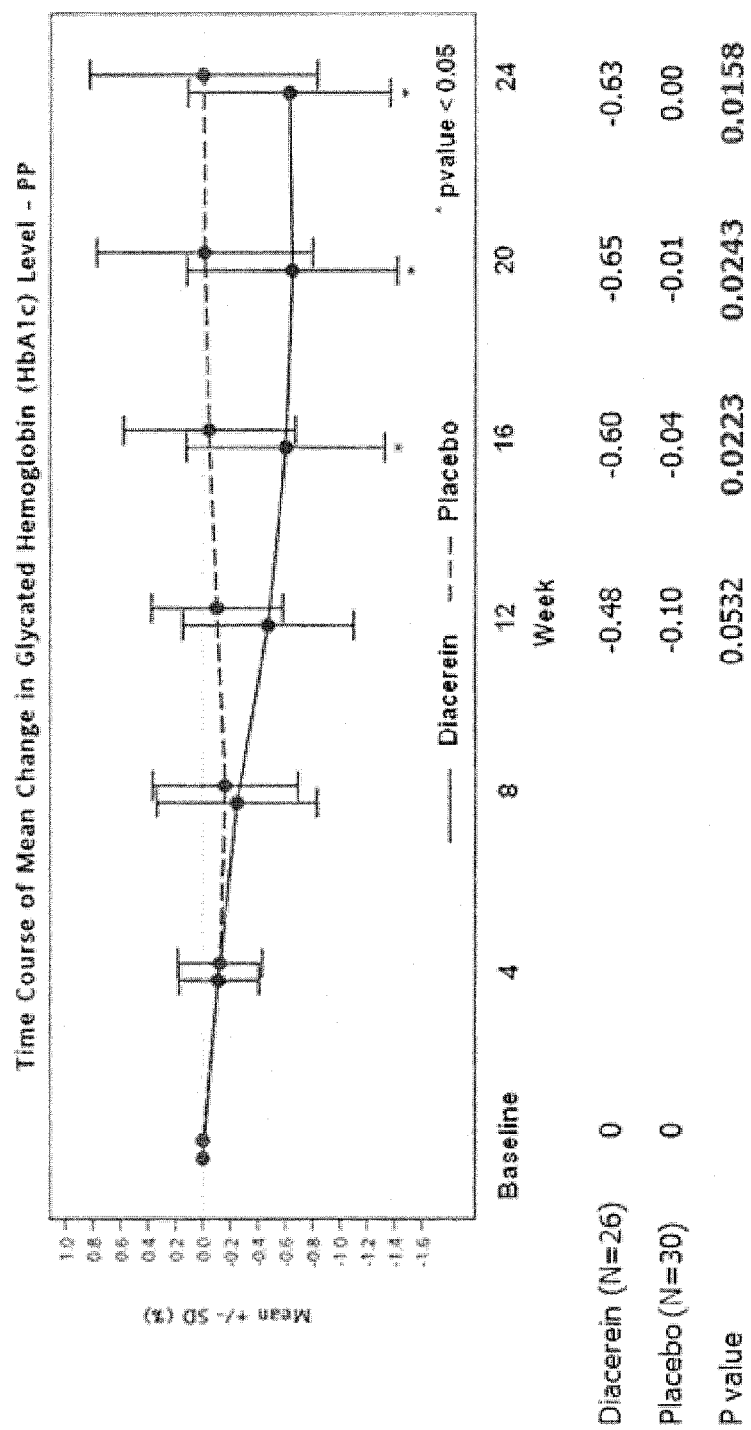
FIG. 1 is a graph demonstrating mean change in patients' glycosylated hemoglobin (HbA1c) levels over the course of treatment with diacerein or placebo.

According to the present invention, diacerein can be used for the treatment of type II diabetes alone or in combination with conventional antidiabetic drugs. Preferably, diacerein can be added to current antidiabetic agents to enhance reactive or synergize functions of the current agents to which the patients already showed an inadequate response.

As used herein, diacerein (4,5-bis(acetyloxy)-9,10-dioxo-2-anthracene carboxylic acid) refers to a compound having the following structure formula:

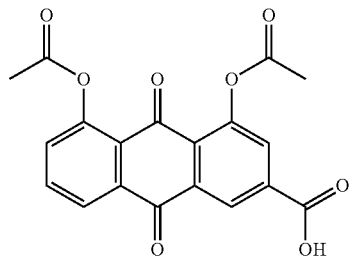 [SMILES: CC(=O)Oc1cccc2c1C(=O)c1c(OC(C)=O)cc(C(=O)O)cc1C2=O]

Pharmaceutically acceptable salts, prodrugs and active metabolites of diacerein are also contemplated for use in this invention. Pharmaceutically acceptable salts include salts of acidic or basic groups. Rhein (9,10-dihydro-4,5-dihydroxy-9,10-dioxo-2-anthracenecarboxylic acid) and monoacetyl-rhein are the known active metabolites of diacerein. A prodrug is a pharmacologically inactive derivative of an active drug that is designed to convert into the active drug through in vivo physiological action, such as hydrolysis, metabolism and the like.

In one embodiment, the invention provides a method of an adjunctive treatment for type II diabetes mellitus comprising administering to a subject with type II diabetes who has an inadequate response to an antidiabetic agent a therapeutically effective amount of diacerein or a pharmaceutically acceptable salt, an analog, a prodrug or an active metabolite thereof.

As used herein, the term "treat" or "treatment" means reversing, alleviating, inhibiting, or slowing the progress of a disease, disorder, or condition to which such term applies, or one or more symptoms of such disease, disorder, or condition.

As used herein, the term "adjunctive treatment" or "add-on treatment" means an additional treatment to a patient who has already received at least one other antidiabetic therapy. A drug used as adjunctive therapy is administered to a patient to make that primary treatment works better.

As used herein, the term "anti-diabetic agents" refers to drugs used to treat diabetes mellitus by lowering glucose levels in the blood. Examples of currently available antidiabetic drugs include, but not limited to, sulfonylurea, biguanides, alpha-glucosidase inhibitors, thiazolidinediones (TZDs), dipeptidyl peptidase-4 inhibitors (DPP-4 inhibitors), nonsulfonylurea insulin secretagogues, glucagon-like peptide-1 analogs (GLP-1 analogs) and insulin. More specifically, the antidiabetic drugs include, but are not limited to metformin, glyburide, glimepiride, glipyride, glipizide, chlorpropamide, gliclazide, acarbose, miglitol, pioglitazone, troglitazone, rosiglitazone, isaglitazone, muraglitizar, peliglitazar, sitagliptin, saxagliptin, vildagliptin, alogliptin, linagliptin, dutogliptin, dutogliptin, repaglinide, nateglinide, mitiglindine, exenatide, liraglutide, albiglutide and insulin. These drugs can be given alone or in combination.

As used herein, the term "subject" includes humans and animals.

Conventionally, subjects diagnosed with type II diabetes are usually given one or more oral antidiabetic agents to control their blood glucose, blood pressure and lipids to minimize the risk of complications.

In one embodiment, the invention provides a method of an adjunctive treatment for type II diabetes mellitus comprising administering to a subject with type II diabetes who has an inadequate response to an antidiabetic agent a therapeutically effective amount of diacerein or a pharmaceutically acceptable salt, an analog, a prodrug or an active metabolite thereof.

According to one embodiment of the adjunctive treatment of the invention, diacerein is added to the antidiabetic agents currently taken by patients. More specifically, the adjunctive treatment of the invention may be employed for lowering blood glucose, decreasing insulin resistance, decreasing glycated hemoglobin A1C (HbA1c), increasing post-prandial insulin levels or decreasing post-prandial glucose excursion.

In one embodiment, type II diabetic patients with insulin resistance, glucose intolerance, hyperglycemia, or hyperinsulinemia that has not been adequately controlled by an antidiabetic therapy with an antidiabetic agent alone or in combination with other antidiabetic agents are suitable for the adjunctive treatment of the invention.

In a preferred embodiment, a subject with type II diabetes who has an inadequate response to an antidiabetic drug (i.e., the patient whose insulin resistance, glucose intolerance, hyperglycemia, or hyperinsulinemia has not been adequately controlled by an antidiabetic therapy) is a patient whose hemoglobin A1c (HbA1c) value is above 7% despite receiving one or more antidiabetic agents. The HbA1c value is the percent hemoglobin with glucose attached, and is an indicator of long-term glycemic control. Preferably, patients whose HbA1c value is between 8 to 10% while receiving at least one antidiabetic drug are particularly suitable for the adjunctive treatment of the invention.

The therapeutically effective amount of diacerein may vary with individual differences in age, weight, extent of diabetes, and the condition of the patient and can be determined by a skilled artisan. In a preferred embodiment of the invention, the therapeutically effective amount of diacerein is within the range of 25 to 200 mg per day. In one embodiment, diacerein or its derivatives (including, but not limited to pharmaceutically acceptable salts, prodrugs, analogs, and active metabolites of diacerein) can be administered once or twice per day. The therapeutically effective amount of the pharmaceutically acceptable salt, analog, prodrug or active metabolite of diacerein is preferably equivalent to 25 to 200 mg of diacerein base per day.

Subjects diagnosed as having type II diabetes mellitus may receive diacerein, its pharmaceutically acceptable salts, analogs, prodrugs, or active metabolites together with one or more antidiabetic drugs to achieve the treatment goals.

The treatment goal may be to lower blood glucose, decrease insulin resistance, decrease glycated hemoglobin A1C (HbA1c), increase post-prandial insulin levels or decrease post-prandial glucose excursion. More specifically, the treatment goals include but are not limited to: (a) HbA1c of 6% to 7.0%; (b) preprandial blood glucose: 4.0 to 6.0 mmol/L (72 to 108 mg/dl) and (c) 2-hour postprandial blood glucose: 5.0 to 8.0 mmol/L (90 to 144 mg/dl).

In one embodiment, the method of an adjunctive treatment for type II diabetes improves kidney functions of the subject. The improvement of kidney functions may be demonstrated through reduction of creatinine clearance in the subject.

In another embodiment, the method of an adjunctive treatment for type II diabetes reduces insulin resistance in the subject. The reduced insulin resistance may be demonstrated through decreasing levels of glycosylated hemoglobin in the subject.

In yet another embodiment, the method of an adjunctive treatment for type II diabetes results in reduction of inflammation cytokines (including but not limited to interleukins and tumor necrosis factors) in the subject. Interleukins include but are not limited to interleukin IL-6 and interleukin IL-12. Tumor necrosis factors include but are not limited to TNF-α.

In yet another embodiment, the invention provides a method of improving glycemic control in a subject receiving at least one antidiabetic agent, said method comprising administering to said subject: a) a therapeutically effective amount of diacerein or a pharmaceutically acceptable salt, an analog, a prodrug, or an active metabolite thereof, and b) said antidiabetic agent.

In one embodiment, the method of improving glycemic control improves kidney functions of the subject. The improvement of kidney functions may be demonstrated through reduction of creatinine clearance in the subject.

In another embodiment, the method of improving glycemic control reduces insulin resistance in the subject. The reduced insulin resistance may be demonstrated through decreasing levels of glycosylated hemoglobin in the subject.

In yet another embodiment, the method of improving glycemic control results in reduction of inflammation cytokines (including but not limited to interleukins and tumor necrosis factors) in the subject. Interleukins include but are not limited to interleukin IL-6 and interleukin IL-12. Tumor necrosis factors include but are not limited to TNF-α.

In one embodiment, type II diabetic patients with insulin resistance, glucose intolerance, hyperglycemia or hyperinsulinemia that has not been controlled by antidiabetic therapy with at least one antidiabetic agent or the combination thereof are suitable for the method of improving glycemic control of the invention. Preferably, patients with type II diabetes who have an inadequate response to an antidiabetic agent are suitable for the method of improving glycemic control of the invention.

In another embodiment, the invention provides a method of a combinational treatment for type II diabetes mellitus comprising administering to a subject in need thereof: a) at least one antidiabetic agent, and b) a therapeutically effective amount of diacerein or a pharmaceutically acceptable salt, an analog, a prodrug or an active metabolite thereof.

In yet another embodiment, the invention provides a method for reducing a side effect of an antidiabetic agent administered to a diabetic patient comprising administering to said patient: a) a therapeutically effective amount of diacerein or a pharmaceutically acceptable salt, an analog, a prodrug, or an active metabolite thereof, and b) said antidiabetic agent.

In yet another embodiment, the invention provides a method for reducing a cardiovascular risk of an antidiabetic agent administered to a diabetic patient comprising administering to said patient: a) a therapeutically effective amount of diacerein or a pharmaceutically acceptable salt, an analog, a prodrug, or an active metabolite thereof, and b) said antidiabetic agent.

When administered to a subject in need thereof, diacerein, its pharmaceutically acceptable salts, analogs, prodrugs, or active metabolites can be prepared as a pharmaceutical composition. Pharmaceutical compositions contemplated for use for the purposes of the present invention can be in the form of a solid, solution, emulsion, dispersion, micelle, liposome and the like. The compositions may be administered using any means known in the art, such as orally, nasally, parenterally, topically, transdermally, or rectally. Preferably, the compositions are adapted for oral administration. For example, the drug can be mixed with suitable excipients for the preparation of tablets, capsules, pellets, troches, lozenges, solutions, powders or granules, suspensions, hard or soft capsules and any other forms suitable for use. The methods for preparing the pharmaceutical compositions and the selection of suitable excipients are readily understood by a skilled person in the art.

The following Example demonstrates some aspects of the invention. The Example is not meant to limit the invention in any way.

EXAMPLE 1

A Randomized, Double-Blind, Placebo-Controlled Study of Diacerein in Patients with Uncontrolled Type 2 Diabetes Mellitus Objectives: To evaluate the efficacy and safety of diacerein for the treatment of type 2 diabetes mellitus (DM).

Primary Endpoints: To compare the efficacy of add-on diacerein with no add-on treatment (placebo) on glycosylated hemoglobin (HbA1c) after 24-week double-blind treatment in type 2 DM patients inadequately controlled by previous antidiabetic therapy.

Subjects: Male or female type 2 DM patients (BMI≦35 kg/m$^2$) on a stable oral hypoglycemic monotherapy for at least 3 months prior to screening visit. The hemoglobin A1c (HbA1c) measurements taken at a screening visit were between 7% and 12%. Patients enrolled in the study were receiving one or more oral antihyperglycemic agents including sulfonylurea, biguanides, alpha-glucosidase inhibitors, thiazolidinediones (TZDs) and nonsulfonylurea insulin secretagogues.

Procedure: This was a randomized, double-blind, parallel comparison study comparing 50 mg diacerein versus placebo in patients with type 2 DM inadequately controlled by previous antidiabetic therapy. The starting dose of diacerein was 50 mg once daily every morning for 4 weeks and could be adjusted up to 50 mg twice daily (morning and evening) if patients had become accustomed to the medication. Patients were screened for eligibility four weeks (week-4) prior to entry at baseline (week 0). During this 4-week screening period, the participants continued their previous antidiabetic therapy, dietary habits and other lifestyle habits. In order to be eligible for randomization following the 4-week screening period, patients must not have experienced hypoglycemia and must have had two fasting plasma glucose (FPG) measurements of between 135 to 250 mg/dL. At the end of the screening period, patients who met eligibility requirements were randomly assigned to receive diacerein 50 mg or placebo twice a day for 24 weeks observation. During treatment/observation period, the previous antidiabetic therapy including the class and/or dosage was not changed. Patients were asked to attend the center on eight occasions (screening, baseline, week 4, 8, 12, 16, 20 and 24) during the trial. The total study duration including the screening period for each patient was 28 weeks. There was a two weeks follow-up period after completion of the treatment/observation. During this follow-up period, patients were followed for adverse events.

Statistical method(s) for efficacy/safety evaluations: The difference (diacerein minus placebo) of HbA1c reduction between the two treatment groups was analyzed by analysis of covariance (ANCOVA) with baseline value as covariate. The corresponding 95% confidence interval was calculated. Within-group changes were also analyzed, with paired t test used to evaluate differences from baseline in each treatment group.

For the efficacy parameters, descriptive statistics were presented by visit. Statistical analysis was performed to assess the mean change from baseline. The area under the concentration-time curve (AUC) was used for evaluating the parameters measured by oral glucose tolerance test.

Adverse events were summarized according to the Medical Dictionary for Regulatory Activities (MedDRA) adverse event dictionary. The tabulations counted the number of patients reporting individual preferred term adverse events and the total number of patients reporting at least one adverse event per system organ class. If appropriate, the incidence of adverse events was compared for each of the two treatment groups using Fisher's Exact test.

Results: This double-blind, parallel-group study involved 76 patients with type 2 diabetes inadequately controlled by current oral antidiabetic therapy (Table 1). Patients were randomly assigned to two treatment groups. One group received diacerein (38 patients), and the other group received placebo (38 patients). Twenty six of 38 patients receiving diacerein completed the study, as did thirty of 38 patients receiving placebo. No patients changed their antidiabetic therapy during the 24-week study period.

TABLE 1

Antidiabetic Medications of All Randomized Subjects

| Regimen Combinations | Diacerein (N = 38) | Placebo (N = 38) |
|---|---|---|
| Monotherapy | 3 | 6 |
| Two Drugs Combinations | 18 | 19 |
| Three Drugs Combinations | 12 | 13 |
| Four Drugs Combinations | 5 | 0 |

Monotherapy: treatment with metformin or sulfonylurea alone
Drug Combinations: treatment with two, three or four oral antidiabetic agents (selected from metformin, sulfonylurea, acarbose, repaglinide, pioglitazone and sitagliptin)

Primary Endpoint: The average absolute difference in HbA1c levels between baseline and 24 weeks was a reduction of 0.63 percentage point in the diacerein group, and no change in the placebo group, yielding a between-group difference of 0.63 percentage point (P=0.0158). See, FIG. 1 which demonstrates mean change from baseline in HbA1c levels.

The number of patients who had any reduction in HbA1c levels at 24 weeks was 20 of 26 patients in the diacerein group, as compared with 15 of 30 patients in the placebo group. HbA1c levels were significantly lower in the diacerein group after 20 weeks than in the placebo group (an absolute reduction of 0.60%; P=0.0223). See, FIG. 1.

Secondary Endpoints:
Glycemia

Figure 2:
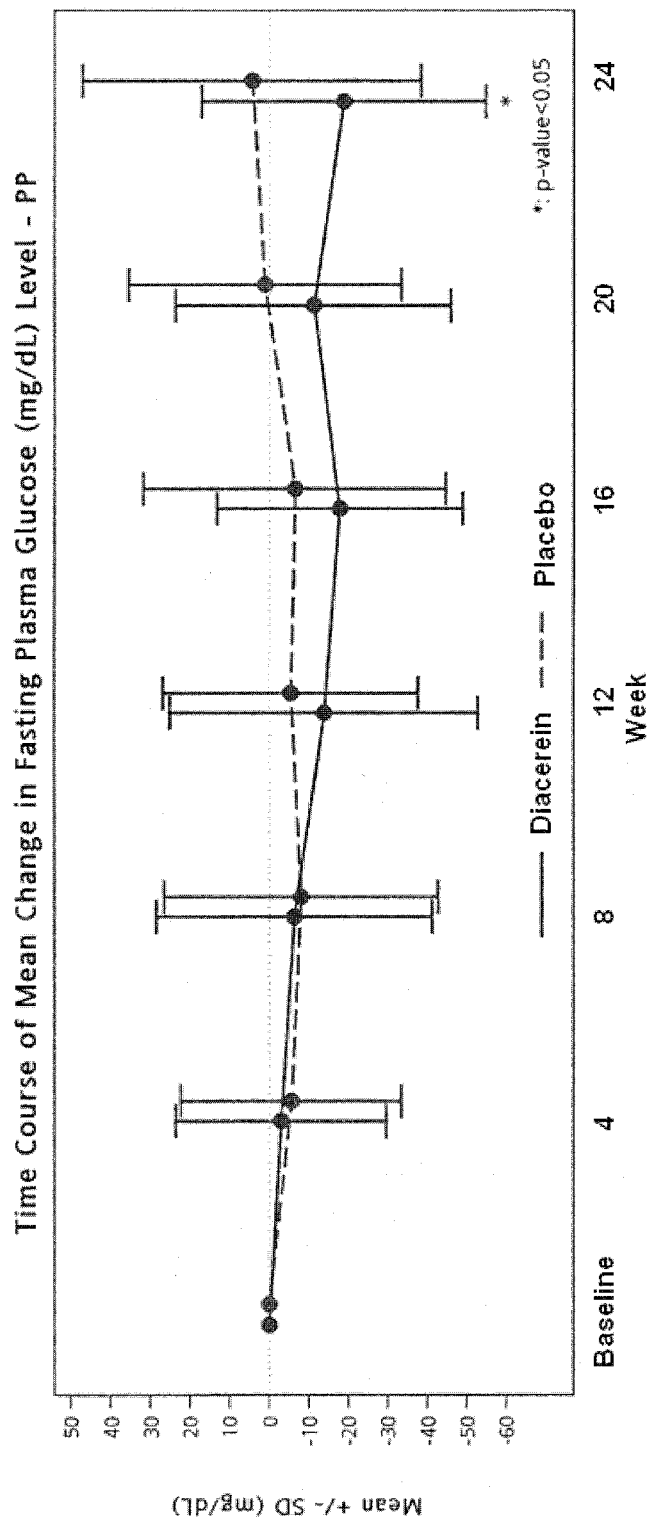
FIG. 2 is a graph demonstrating mean change in patients' fasting plasma glucose levels over the course of treatment with diacerein or placebo.

Fasting plasma glucose levels were consistently lower in the diacerein group than in the placebo group at 24 weeks. See, FIG. 2.

Beta Cell Function

Figure 3:
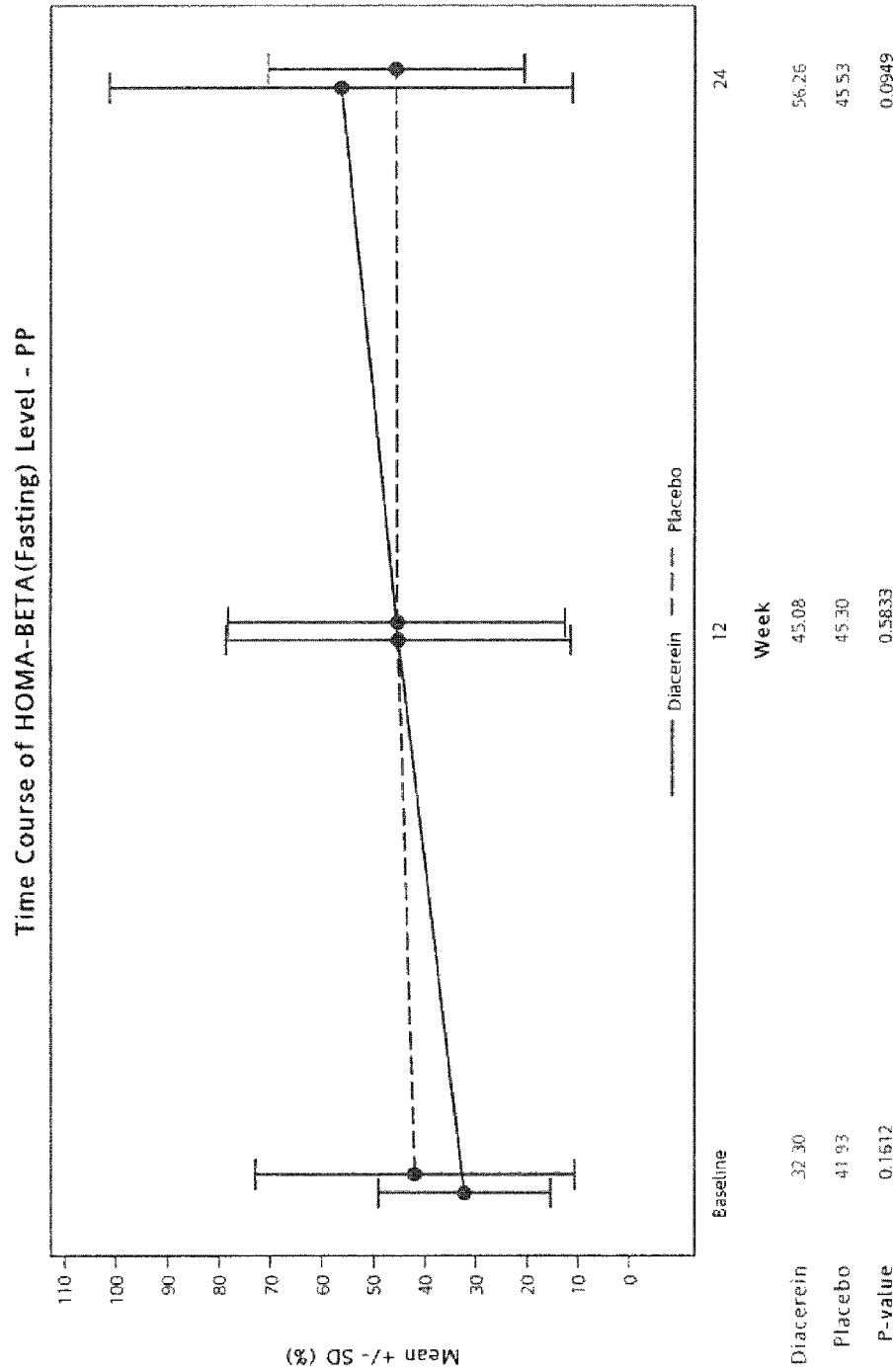
FIG. 3 is a graph demonstrating mean change in patients' homeostatic model assessment (HOMA) beta-cell function levels over the course of treatment with diacerein or placebo.

A continual improvement in the homeostatic model assessment (HOMA) beta cell function (HOMA-BETA) was observed in the diacerein group, but not in the placebo group. As FIG. 3 demonstrates, at week 24, the same unit of glucose induced more insulin secretion in the diacerein patients than in the placebo patients (Diacerein: 56.26 vs. Placebo: 45.53). The within-group change from baseline in HOMA-BETA was significant in the diacerein group, but not in the placebo group.

Cardiovascular Safety Endpoints

Figure 4:
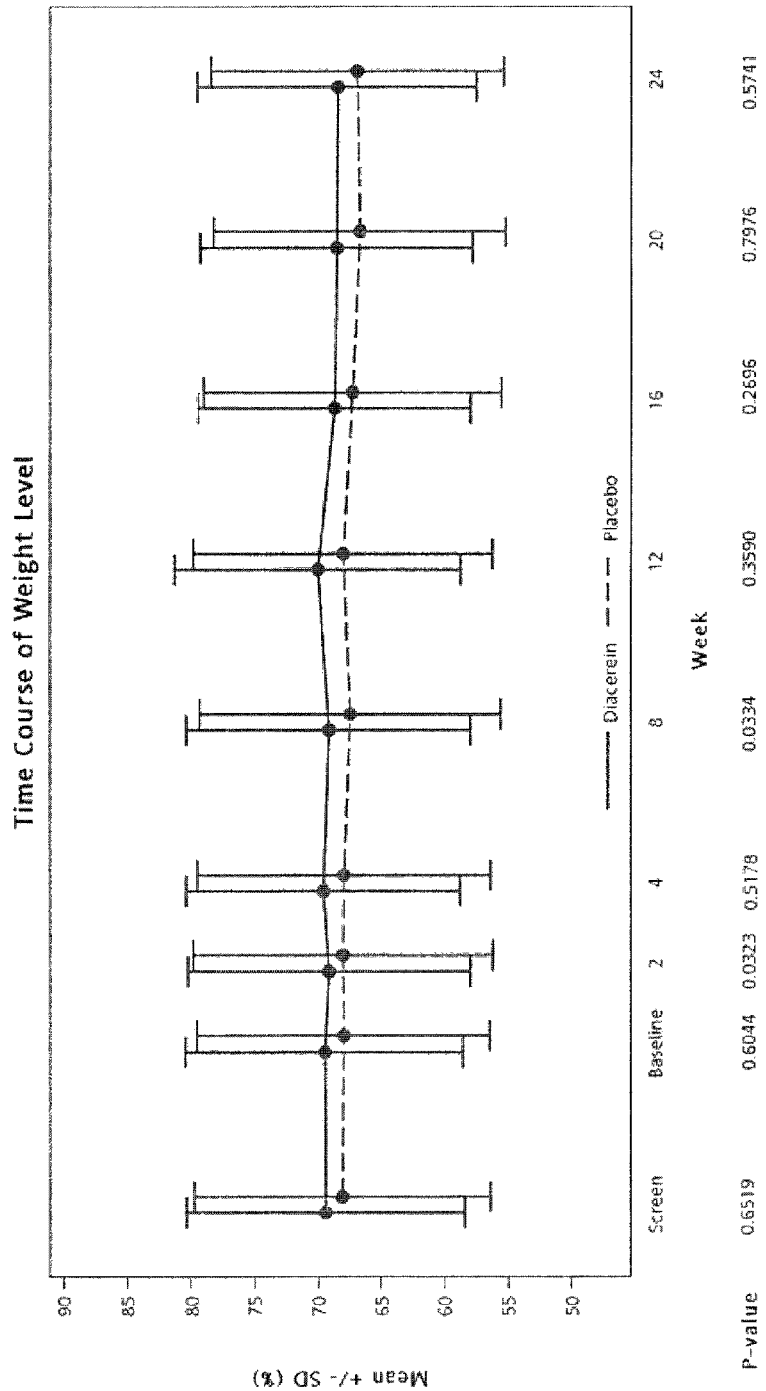
FIG. 4 is a graph demonstrating mean change in patients' body weight levels over the course of treatment with diacerein or placebo.

There were no statistically significant differences between the treatment groups in body weight (FIG. 4), blood pressure (Tables 2 and 3), pulse rate (Table 4) and lipid profiles (Tables 5 to 8) between baseline levels and levels at week 24. The results of cardiovascular safety endpoints indicated that adding diacerein to current anti-diabetic treatment did not increase the risks of heart attack and cardiovascular disorders.

TABLE 2

Cardiovascular (CV) Safety Endpoints-Systolic blood pressure

| Treatment Group | Statistics | Baseline | Week 24 |
|---|---|---|---|
| DIACEREIN | N | 37 | 28 |
| | Mean ± SD | 131.41 ± 12.56 | 130.32 ± 16.85 |
| | Change | — | −0.25 ± 14.38 |
| Placebo | N | 38 | 32 |
| | Mean ± SD | 130.32 ± 13.00 | 131.56 ± 13.12 |
| | Change | — | 2.78 ± 11.93 |
| | P-value | 0.6849 | 0.5769 |

TABLE 3

CV Safety Endpoints-diastolic blood pressure

| Treatment Group | Statistics | Baseline | Week 24 |
|---|---|---|---|
| DIACEREIN | N | 37 | 28 |
| | Mean ± SD | 80.14 ± 8.95 | 78.86 ± 8.20 |
| | Change | — | −1.14 ± 8.78 |
| Placebo | N | 38 | 32 |
| | Mean ± SD | 79.32 ± 8.11 | 81.72 ± 9.36 |
| | Change | — | 3.03 ± 6.56 |
| | P-value | 0.5772 | 0.0663 |

TABLE 4

CV Safety Endpoints-pulse rate

| Treatment Group | Statistics | Baseline | Week 24 |
|---|---|---|---|
| DIACEREIN | N | 37 | 28 |
| | Mean ± SD | 77.11 ± 11.85 | 77.18 ± 10.22 |
| | Change | — | 1.46 ± 9.00 |
| Placebo | N | 38 | 32 |
| | Mean ± SD | 80.68 ± 13.11 | 80.50 ± 9.41 |
| | Change | — | 0.06 ± 13.05 |
| | P-value | 0.2435 | 0.5245 |

TABLE 5

CV Safety Endpoints-Total Cholesterol

| Treatment Group | Statistics | Baseline | Week 24 |
|---|---|---|---|
| DIACEREIN | N | 37 | 28 |
| | Mean ± SD | 177.81 ± 46.25 | 164.61 ± 30.09 |
| | Change | — | −8.46 ± 32.20 |
| Placebo | N | 38 | 32 |
| | Mean ± SD | 172.87 ± 44.88 | 163.56 ± 28.68 |
| | Change | — | −14.72 ± 37.96 |
| | P-value | 0.6693 | 0.5130 |

TABLE 6

CV Safety Endpoints-Triglyceride

| Treatment Group | Statistics | Baseline | Week 24 |
|---|---|---|---|
| DIACEREIN | N | 37 | 28 |
| | Mean ± SD | 169.57 ± 109.91 | 159.18 ± 97.07 |
| | Change | — | −7.57 ± 98.79 |

TABLE 6-continued

CV Safety Endpoints-Triglyceride

| Treatment Group | Statistics | Baseline | Week 24 |
|---|---|---|---|
| Placebo | N | 38 | 32 |
| | Mean ± SD | 170.00 ± 100.92 | 154.50 ± 95.29 |
| | Change | — | −25.88 ± 72.37 |
| | P-value | 0.9842 | 0.4668 |

TABLE 7

CV Safety Endpoints-HDL

| Treatment Group | Statistics | Baseline | Week 24 |
|---|---|---|---|
| DIACEREIN | N | 37 | 28 |
| | Mean ± SD | 44.55 ± 14.23 | 42.25 ± 10.40 |
| | Change | — | −0.96 ± 10.27 |
| Placebo | N | 38 | 32 |
| | Mean ± SD | 39.67 ± 10.86 | 40.93 ± 9.17 |
| | Change | — | 1.06 ± 6.35 |
| | P-value | 0.0923 | 0.8447 |

TABLE 8

CV Safety Endpoints-LDL

| Treatment Group | Statistics | Baseline | Week 24 |
|---|---|---|---|
| DIACEREIN | N | 37 | 28 |
| | Mean ± SD | 101.43 ± 29.27 | 91.64 ± 27.28 |
| | Change | — | −6.09 ± 19.75 |
| Placebo | N | 38 | 32 |
| | Mean ± SD | 98.42 ± 37.13 | 92.42 ± 22.29* |
| | Change | — | −8.94 ± 32.54 |
| | P-value | 0.7052 | 0.7893 |

Adverse Effects: During the study period, at least one adverse effect (AE) was reported by 20 (54.1%) patients in the diacerein group and 18 (47.4%) of patients in the placebo group. No statistically significant difference between the two groups was detected in the incidence of patients complaining of adverse events. The frequently reported AEs in both groups were upper respiratory tract infection and diarrhea. In particular, symptomatic hypoglycemia was not observed, even in patients with a marked improvement in HbA1c levels.

The invention claimed is:

1. A method of an adjunctive treatment for type II diabetes mellitus comprising the steps of: a) selecting a human patient population comprising human patients with type II diabetes mellitus receiving at least one antidiabetic agent and whose hemoglobin A1c value is above 7%; and b) administering to a member of said human patient population therapeutically effective amount of diacerein, a pharmaceutically acceptable salt thereof, rhein or monoacetylrhein.

2. The method of claim 1, wherein said therapeutically effective amount of diacerein is from 25 to 200 mg per day.

3. The method of claim 1, wherein said therapeutically effective amount of said pharmaceutically acceptable salt, rhein or monoacetylrhein is equivalent to between 25 and 200 mg of diacerein base per day.

4. The method of claim 1, wherein said antidiabetic agent is at least one agent selected from the group consisting of sulfonylurea, a biguanide, an alpha-glucosidase inhibitor, a thiazolidinedione, a peroxisome proliferator-activated receptor agonist, a dipeptidyl peptidase-4 inhibitor, a nonsulfonylurea insulin secretagogue, a glucagon-like petide-1 analog and insulin.

5. The method of claim 1, wherein said antidiabetic agent is at least one agent selected from the group consisting of metformin, glyburide, glimepiride, glipyride, glipizide, chlorpropamide, gliclazide, acarbose, miglitol, pioglitazone, troglitazone, rosiglitazone, isaglitazone, muraglitizar, peliglitazar, sitagliptin, saxagliptin, vildagliptin, alogliptin, linagliptin, dutogliptin, dutogliptin, repaglinide, nateglinide, mitiglindine, exenatide, liraglutide, albiglutide and insulin.

6. The method of claim 1, wherein said member of said human patient population is a type II diabetic patient with a condition selected from the group consisting of insulin resistance, glucose intolerance, hyperglycemia, or hyperinsulinemia.

7. The method of claim 1, wherein said method improves kidney functions of said member of said human patient population.

8. The method of claim 1, wherein said method reduces insulin resistance of said member of said human patient population.

9. The method of claim 1, wherein said method results in reduction of inflammation cytokines.

10. The method of claim 9, wherein said inflammation cytokines are selected from interleukins and tumor necrosis factors.

11. The method of claim 10, wherein said interleukins are selected from the group consisting of interleukin IL-6 and interleukin IL-12.

12. The method of claim 10, wherein said tumor necrosis factors comprise TNF-α.

13. A method of improving glycemic control in a human subject receiving an antidiabetic agent comprising the steps of: a) selecting a human patient population comprising human patients with type II diabetes mellitus receiving at least one antidiabetic agent and whose hemoglobin A1c value is above 7%; and b) administering to a member of said human patient population: 1) a therapeutically effective amount of diacerein, or a pharmaceutically acceptable salt thereof, rhein or monoacetylrhein, and 2) one or two of said antidiabetic agents, wherein glycemic control is improved in said member.

14. The method of claim 13, wherein said therapeutically effective amount of diacerein is from 25 to 200 mg per day.

15. The method of claim 13, wherein said therapeutically effective amount of said pharmaceutically acceptable salt, rhein or monoacetylrhein is equivalent to between 25 and 200 mg of diacerein base per day.

16. The method of claim 13, wherein said antidiabetic agent is one or more agents selected from the group consisting of sulfonylurea, a biguanide, an alpha-glucosidase inhibitor, a thiazolidinedione, a peroxisome proliferator-activated receptor agonist, a dipeptidyl peptidase-4 inhibitor, a nonsulfonylurea insulin secretagogue, a glucagon-like petide-1 analog and insulin.

17. The method of claim 13, wherein said member of said human patient population is a type II diabetic patient with a condition selected from the group consisting of insulin resistance, glucose intolerance, hyperglycemia, or hyperinsulinemia.

18. The method of claim 13, wherein said method improves kidney functions of said member of said human patient population.

19. The method of claim 13, wherein said method reduces insulin resistance of said member of said human patient population.

20. The method of claim 13, wherein said method results in reduction of inflammation cytokines.

21. The method of claim 20, wherein said inflammation cytokines are selected from interleukins and tumor necrosis factors.

22. The method of claim 21, wherein said interleukins are selected from the group consisting of interleukin IL-6 and interleukin IL-12.

23. The method of claim 21, wherein said tumor necrosis factors comprise TNF-α.

* * * * *